US008144888B2

(12) United States Patent
Berkhoff et al.

(10) Patent No.: US 8,144,888 B2

(45) Date of Patent: Mar. 27, 2012

(54) FILTER APPARATUS FOR ACTIVELY REDUCING NOISE

(75) Inventors: Arthur Perry Berkhoff, Doetinchem (NL); Gerard Nijsse, Monster (NL)

(73) Assignee: Nederlandse Organisatie voor toegepastnatuurwetenschappelijk onderzoek TNO (NL)

( * ) Notice: Subject to any disclaimer, the term of this patent is extended or adjusted under 35 U.S.C. 154(b) by 737 days.

(21) Appl. No.: 12/095,819

(22) PCT Filed: Dec. 4, 2006

(86) PCT No.: PCT/NL2006/000610

§ 371 (c)(1), (2), (4) Date: Dec. 18, 2008

(87) PCT Pub. No.: WO2007/064203

PCT Pub. Date: Jun. 7, 2007

(65) Prior Publication Data

US 2010/0150369 A1 Jun. 17, 2010

(30) Foreign Application Priority Data

Dec. 2, 2005 (EP) .................................... 05077758

(51) Int. Cl.

*A61F 11/06* (2006.01)

*G10K 11/16* (2006.01)

*H03B 29/00* (2006.01)

(52) U.S. Cl. .................................... 381/71.11; 381/71.1

(58) Field of Classification Search ................. 381/71.1, 381/71.8–71.12

See application file for complete search history.

(56) References Cited

U.S. PATENT DOCUMENTS 5,325,437 A * 6/1994 Doi et al. ..................... 381/71.9

5,524,057 A * 6/1996 Akiho et al. ................. 381/94.7

(Continued)

FOREIGN PATENT DOCUMENTS

CA 2356222 6/2000

(Continued)

OTHER PUBLICATIONS

"A Preconditioned LMS Algorithm for Rapid Adaptation of Feedforward Controllers"; Elliott S. J. et al., Acoustics, Speech, and Signal Processing, vol. 2 pp. 845-848, 2000 IEEE International Conference on Jun. 5-9, 2000, Piscataway, NJ, USA.

(Continued)

*Primary Examiner* — Anh Mai

*Assistant Examiner* — Alexander Talpalatskiy

(74) *Attorney, Agent, or Firm* — Altera Law Group, LLC

(57) ABSTRACT

A filter apparatus for reducing noise from a primary noise source, comprising a secondary source signal connector for generating secondary noise to reduce said primary noise and a sensor connector for connecting to a sensor for measuring said primary and secondary noise as an error signal. A first control filter is arranged to receive a reference signal and calculate a control signal for the secondary source signal. A second control filter is arranged to receive a delayed reference signal and calculate an auxiliary control signal; wherein an adaptation circuit is arranged to adapt said second control filter while receiving an error signal as a sum of the auxiliary control signal and an auxiliary noise signal. The auxiliary noise signal is constructed from a difference of the delayed filtered error signal and a delayed control signal. The first control filter is updated by a copy of said updated second control filter.

7 Claims, 6 Drawing Sheets

U.S. PATENT DOCUMENTS

| | | | | |
|---|---|---|---|---|
| 5,602,929 | A | 2/1997 | Popovich | |
| 5,745,580 | A * | 4/1998 | Southward et al. | 381/71.1 |
| 5,940,519 | A * | 8/1999 | Kuo | 381/71.11 |
| 5,953,380 | A * | 9/1999 | Ikeda | 375/346 |
| 5,991,418 | A * | 11/1999 | Kuo | 381/71.11 |
| 6,192,133 | B1 * | 2/2001 | Enamito et al. | 381/71.5 |
| 6,266,422 | B1 * | 7/2001 | Ikeda | 381/71.11 |
| 6,285,768 | B1 * | 9/2001 | Ikeda | 381/71.11 |
| 6,418,227 | B1 * | 7/2002 | Kuo | 381/71.11 |
| 6,487,295 | B1 * | 11/2002 | Lofgren et al. | 381/71.12 |
| 6,516,050 | B1 * | 2/2003 | Tasaki et al. | 379/3 |
| 6,831,986 | B2 * | 12/2004 | Kates | 381/312 |
| 6,847,721 | B2 * | 1/2005 | Zhang et al. | 381/71.11 |
| 6,963,649 | B2 * | 11/2005 | Vaudrey et al. | 381/94.7 |
| 2002/0003887 | A1 * | 1/2002 | Zhang et al. | 381/71.1 |
| 2005/0175187 | A1 * | 8/2005 | Wright et al. | 381/71.12 |
| 2007/0253566 | A1 * | 11/2007 | Shako et al. | 381/71.1 |

FOREIGN PATENT DOCUMENTS

| | | |
|---|---|---|
| WO | WO 98/48508 | 10/1998 |
| WO | WO 01/35175 | 5/2001 |

OTHER PUBLICATIONS

"Optimal Controllers and Adaptive Controllers for Multichannel Feedforward Control of Stochastic Disturbances"; Elliott S. J., vol. 48, No. 4, pp. 1053-1060, IEEE Transactions on Signal Processing, IEEE Service Center, Apr. 4, 2000, New York, NY, USA.

"Multichannel Adaptive Least Squares Lattice Filters for Active Noise Control"; Lopes et al, Digital Signal Processing and Its Applications, Mar. 2003.

"Computational Load Reduction of Fast Convergence Algorithms for Multichannel Active Noise Control", Bouchard M. et al., Signal Processing, vol. 83, No. 1, pp. 121-134, Jan. 2003, Amsterdam, The Netherlands.

"Increasing the Robustness of a Preconditioned Filtered-X LMS Algorithm"; Fraanje R. et al, Signal Processing Letters, IEEE, vol. 11, No. 2, pp. 285-288, Feb. 2004.

Bouchard M. and Yu Feng: "Inverse Structure for Active Noise Control and Combined Active Noise Control/Sound Reproduction Systems", IEEE Transactions on Speech and Audio Processing vol. 9, No. 2, Feb. 1999.

Douglas S.C.: "Fast exact filtered-X LMS and LMS algorithms for multichannel active noise control", Department of Electrical Engineering, University of Utah, Salt Lake City, UT 84112 USA.

Wan Eric A: "Adjoint LMS: an effective alternative to the filtered-X LMS and multiple error LMS algorithms", IEEE International Conf. on Acoustics, Speech and Signal Processing, ICASPP96, 1996.

Bjarnason Elias: "Analysis of the Filtered-X LMS Algorithm", IEEE Transactions on Speech and Audio Processing, vol. 3, No. 6, Nov. 1995.

Seron Maria M., Braslaysky Julio H., Goodwin Graham C.: "Fundamental Limitations in Filtering and Control", School of Electrical Engineering and Computer Science, the University of Newcastle, Callaghan, New South Wales 2308, Australia, ISBN 3-540-76126-8, 1997.

* cited by examiner

FILTER APPARATUS FOR ACTIVELY REDUCING NOISE

FIELD OF INVENTION

The invention relates to a filter apparatus for actively reducing noise from a primary noise source, applying a filtered-error scheme.

Such a filter apparatus typically implements a so called secondary path wherein an actuator is fed with control signals to provide a secondary source that is added to the primary source providing noise to be reduced. The resultant sensed noise is measured by a microphone and fed back into the filter apparatus as an error signal. The filter apparatus comprises a control filter for providing a control signal based on an input reference signal and a time-reversed model of the secondary path formed as the open loop transfer path between the control signal and the sensed resultant error signal. The input reference signal is coherent with the primary noise, for example by providing a signal that is physically derived from the primary noise source, while other sources, in particular the secondary source have a relatively small contribution.

Accordingly, the conventional filter apparatus comprises a secondary source signal connector for connecting to at least one secondary source, such as a loudspeaker, wherein the secondary source generates secondary noise to reduce the primary noise. A sensor connector is provided for connecting to at least one sensor, such as a microphone, for measuring the primary and secondary noise as an error signal. The error signal is delayed and filtered by a time reversed secondary path filter, which is a time-reversed and transposed version of the secondary path as formed by the open loop transfer path between the control signal and the sensed resultant error signal. Accordingly a delayed filtered error signal is provided. An adaptation circuit is arranged to adapt the control filter based on a delayed reference signal and an error signal derived from the delayed filtered error signal. The adaptation circuit can be a least mean square circuit, known in the art.

One of the problems relating to these filters is that they rely on future data, i.e. that they are non-causal. This means that the filtering can only be applied with a delay in the time reversed model of the transfer path between actuators and error sensors. Hence it is difficult to obtain stable filtering, especially in non-stable noise environments due to a degraded convergence of the adaptive filter. This results in a sub optimal performance of the filter so that noise is not reduced in an optimal way. In "Optimal Controllers and Adaptive Controllers for Multichannel Feedforward Control of Stochastic Disturbances", by Stephen J. Elliott, IEEE Vol 48, No. 4, April 2000, an improved version is described of the hereabove discussed filter arrangement, implementing a so-called post-conditioned filtered-error adaptive control scheme. In this scheme the convergence rate is improved by incorporating an inverse of the secondary path between the control filter and the secondary path as a postconditioning filter. In order to ensure stability of such an inverse, only a minimum-phase part of the transfer function is inverted. However, a shortcoming of the system described in this publication is that the convergence rate still suffers from delays in the secondary path.

The invention has as an object to provide a filter apparatus applying a filtered-error scheme, wherein an improved convergence is attained.

To this end, the invention provides a filter apparatus according to the features of claim 1. In particular, the filter apparatus according to the invention, comprises a second control filter arranged to receive a delayed reference signal and calculate an auxiliary control signal. The adaptation circuit is arranged to adapt the second control filter while receiving an error signal as a sum of said auxiliary control signal and an auxiliary noise signal. The auxiliary noise signal is constructed from a difference of the delayed filtered error signal and the delayed control signal. The adaptation circuit is arranged to adapt the first control filter by a copy of said updated second control filter.

Accordingly, the control values of the control filter are provided by an adaptation loop without delay, providing an improved convergence.

BRIEF DESCRIPTION OF SEVERAL VIEWS OF THE DRAWINGS

The invention will be further elucidated with reference to the drawing. In the drawing.

DETAILED DESCRIPTION OF THE INVENTION

Figure 1:
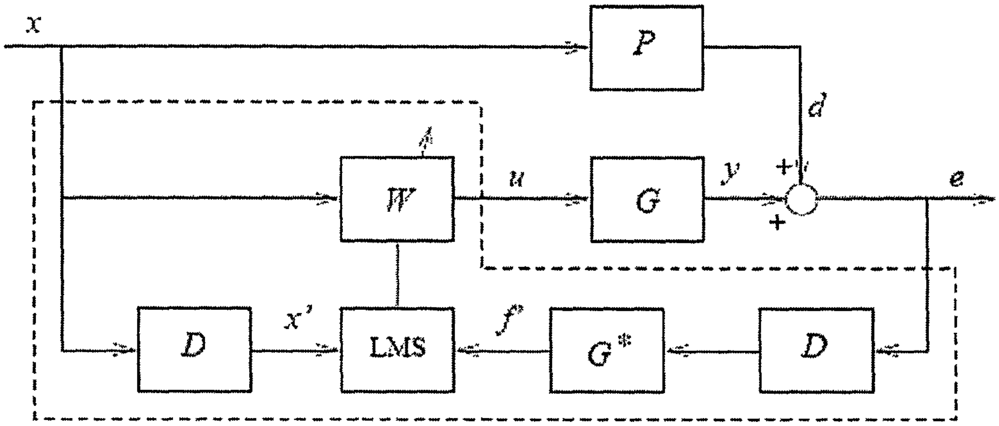
FIG. 1 illustrates a prior art filter apparatus implementing a prior art filtered-error adaptive control scheme.

A block diagram of a conventional filtered-error scheme can be found in FIG. 1. The parts of the diagram which constitute the controller are indicated by a dashed line. All signals are assumed to be stationary. In this scheme, x is the K×1-dimensional reference signal and d is the L×1-dimensional primary disturbance signal, which is obtained from the reference signal by the L×K dimensional transfer function P(z). The goal of the algorithm is to add a secondary signal y to the primary disturbance signal d such that the total signal is smaller than d in some predefined sense. The signal y is generated by driving actuators with the M×1-dimensional driving signal u. The transfer function between u and y is denoted as the L×M-dimensional transfer function G(z), the secondary path. The actuator driving signals u are generated by passing the reference signal x through an M×K-dimensional transfer function W(z) which is implemented by an M×K-dimensional matrix of Finite Impulse Response control filters. The i-th coefficients of this FIR matrix are denoted as the M×K matrix $W_i$. The transfer function matrices $W_i$ are tuned in such a way that the error signal e=d+y is minimum. This tuning is obtained with the least-mean square (LMS) algorithm, which in FIG. 1, is implemented by modifying the control filters $W_i$ at each sample n according to the update rule $$W_i(n+1)=W_i(n)-\alpha f'(n)x'^T(n-i) \tag{1}$$

where T denotes matrix transpose and where x'(n) is a delayed version of the reference signal such that $$x'(z)=D_K(z)x(z) \tag{2}$$

in which $D_K(z)$ is a K×K-dimensional matrix delay operator resulting in a delay of J samples:

$$D_K(z)=z^{-J}I_K(3) \tag{3}$$

and in which f'(n) is a filtered and delayed version of the error signal, such that $$f'(z)=G^*(z)D_L(z)e(z) \quad (4)$$

In Eq. (4) the filtering is done with the adjoint G*(z), which is the time-reversed and transposed version of the secondary path G(z), i.e. $G^*(z)=G^T(z^{-1})$. The adjoint G*(z) is anti-causal and has dimension M×L. The delay for the error signal, and consequently also the delay for the reference signal, is necessary in order to ensure that the transfer function G*(z) $D_L(z)$ is predominantly causal. The convergence coefficient α controls the rate of convergence of the adaptation process, which is stable only if the convergence coefficient is smaller than a certain maximum value.

An advantage of the filtered-error algorithm as compared to the filtered-reference algorithm [2] is that computational complexity is smaller for multiple reference signals [3], i.e. if K>1. A disadvantage of the filtered-error algorithm as compared to the filtered-reference algorithm is that the convergence speed is smaller due to the increased delay in the adaptation path, which requires the use of a lower value of the convergence coefficient α in order to maintain stability.

One of the reasons for a possible reduced convergence rate of the algorithm of FIG. 1 is the frequency dependence of the secondary path G(z) as well as the interaction between the individual transfer functions in G(z). The convergence rate can be improved by incorporating an inverse of the secondary path between the control filter W(z) and the secondary path G(z) [4]. In order to ensure stability of such an inverse, only the minimum-phase part $G_o(z)$ of G(z) is to be inverted. The secondary path is written as $$G(z)=G_i(z)G_o(z) \quad (5)$$

where the following properties hold:

$$G^*(z)G(z)=G^*_o(z)G_o(z) \quad (6)$$

$$G_i^*(z)G_i(z)=I_M \quad (7)$$

Assuming that the number of error signals is at least as large as the number of actuators, i.e. L≧M, the transfer function $G_i(z)$ has dimensions L×M and the transfer function $G_o(z)$ has dimensions M×M. The extraction of the minimum-phase part and the all-pass part is performed with so-called inner-outer factorization [5]. A control scheme in which such an inverse $G^{-1}{}_o(z)$ is used can be found in FIG. 2. The update rule for the control filters $W_i$ in FIG. 2 is $$W_i(n+1)=W_i(n)-\alpha e'(n)x'^T(n-i) \quad (8)$$

Figure 2:
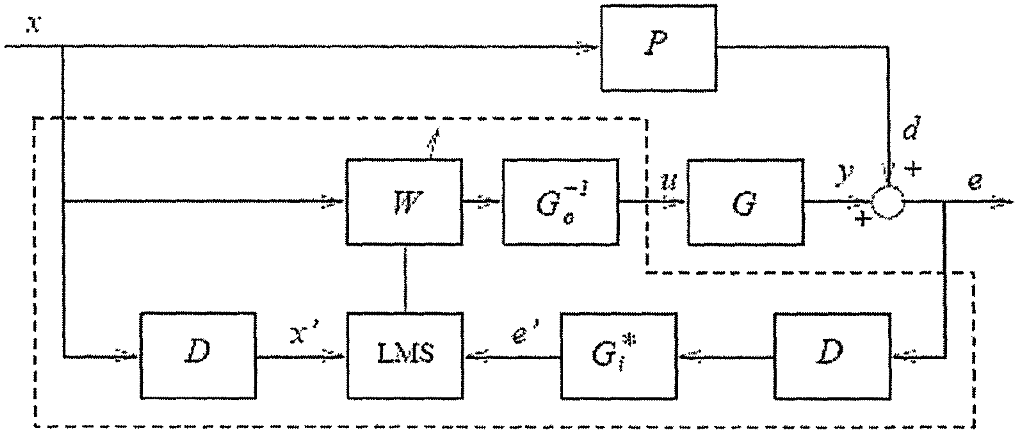
FIG. 2 illustrates a prior art filter apparatus implementing a postconditioned filtered-error adaptive control scheme.

Indeed, if the magnitude of the frequency response of G(z) varies considerably and/or if there is strong interaction between the different channels of G(z) then the convergence rate of the scheme of FIG. 2 can be significantly better than that of FIG. 1. In FIG. 2, the filtered error signal is denoted with e'(n) in order to emphasize that the frequency response magnitude of the filtered error signal has a close correspondence with the real error signal e(n). It should be noted however that e(n) is an L×1 dimensional signal, while e'(n) is an M×1-dimensional signal.

A shortcoming of the scheme of FIG. 2 is that the convergence rate still suffers from delays in the secondary path. The actual cause of this slow convergence rate is that any modification of the controller W operates through the secondary path, including its delays, on the error signal e. Therefore the result of a modification to the controller will be observed only after the delay caused by the secondary path. This makes a rather conservative adaptation strategy necessary, which results in slow adaptation rates.

In order to be able to suggest an improved scheme, an analysis is made of the path which causes the reduced convergence rate, i.e. the path between the output of the control filter W and the LMS block. In particular, the signal e'(z) can be written as $$e'(z)=G_i^*(z)D_L(z)[d(z)+G(z)G^{-1}{}_o(z)W(z)x(z)] \quad (9)$$

Introducing the M×M-dimensional matrix $D_M(z)$ having a delay which is identical to that of the L×L matrix $D_L(z)$, Eq. (9) can be rearranged as $$e'(z)=G_i^*(z)D_L(z)d(z)+D_M(z)G^*_i(z)G(z)G^{-1}{}_0(z)W(z)x(z) \quad (10)$$

Using Eqs. (5) and (7), e'(z) can be expressed as $$e'(z)=d'(z)+y'(z) \quad (11)$$

where the auxiliary disturbance signal d'(z) is given by $$d'(z)=G^*_i(z)D_L(z)d(z) \quad (12)$$

and where the delayed preconditioned control output y'(z) is $$y'(z)=D_M(z)W(z)x(z) \quad (13)$$

From the latter equation, it can be seen that the transfer function between the output of W(z) and y'(z) is a simple delay $D_M(z)$. An auxiliary control output y''(z)=y'(z) is defined by $$y''(z)=W(z)D_K(z)x(z) \quad (14)$$

where $D_K(z)$ is a K×K dimensional matrix having the same delay as $D_M(z)$. In the latter case there is no delay anymore between the controller W(z) and y''(z). In order to be able to realize the above the signal e''(z)=e'(z) is introduced by noting that y'(z)=y''(z):

$$e''(z)=d'(z)+y''(z) \quad (15)$$

Since d'(z) is not directly available it should be reconstructed. Reconstruction of d'(z) is possible using Eq. (11):

$$d'(z)=e'(z)-y'(z) \quad (16)$$

where, according to Eq. (13), y'(z) can be obtained as a delayed version of the output of W(z). Using $D_K(z)x(z)=x'(z)$, which quantity is already available from the schemes of FIGS. 1 and 2 as an input of the LMS block, the auxiliary control output y'' can be written as $$y''(z)=W(z)x(z) \quad (17)$$

The final result is $$e''(z)=d'(z)+W(z)x'(z) \quad (18)$$

Figure 3:
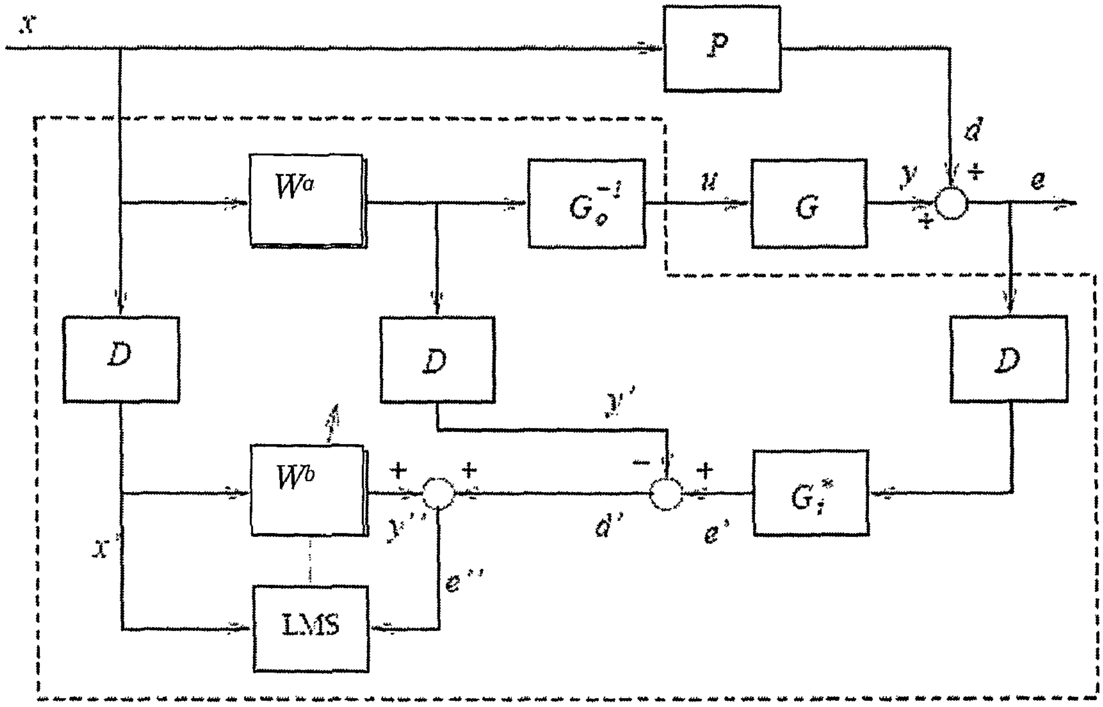
FIG. 3 illustrates an embodiment of a filter apparatus according to the invention, implementing a modified filtered-error adaptive control scheme.

The term y''(z)=W(z)x'(z) can be obtained by adding a second set of control filters $W^b(z)$, which now operate on the delayed reference signals x'(z). A block diagram based on the use of Eq. (18) can be found in FIG. 3. It can be seen that an additional processing of delayed reference signals x'(z) by $W^a(z)$ is necessary. Apart from that, the computational complexity is similar to the postconditioned LMS algorithm of FIG. 2 because the additional delay blocks only require some additional data storage. The update rule for the control filters $W^b{}_i$ in FIG. 3 is $$W^b{}_i(n+1)=W^b{}_i(n)-\alpha e''(n)x'^T(n-i) \quad (19)$$

Control filter $W^a$ is then updated according to the updated control filters $W^b{}_i$.

Regularization of the Outer-Factor Inverse

The inversion of the outer factor $G_o(z)$ may be problematic if the secondary path G(z) contains zeros or near-zeros. Then the inverse $G^{-1}{}_o(z)$ of the outer factor can lead to very high gains and may lead to saturation of the control signal u(n).

Therefore regularization of the outer factor is necessary. A rather straightforward approach for regularization is to add a small diagonal matrix $\beta I_M$ to the transfer matrix G(z), such that the modified secondary path becomes $\tilde{G}(z)=G(z)+\beta\, I_M$, leading to a modified outer factor $\tilde{G}_o(z)$. Apart from the restriction that G(z) should be square, a disadvantage is that the corresponding modified inner factor has to obey $\tilde{G}_i(z)\tilde{G}_o(z)=\tilde{G}(z)$, i.e. $\tilde{G}_i(z)=\tilde{G}(z)\tilde{G}^{-1}_o(z)$, in order to guarantee validity of the filtered-error scheme. In general, such a modified inner factor is no longer all-pass, i.e. $\tilde{G}_i^*(z)\tilde{G}_i(z)\neq I_M$. Then, the derivation of the modified filtered-error scheme is no longer valid since it relies on the inner-factor being all-pass. Similar considerations hold for the use of $\tilde{G}(z)=G_o(z)+\beta\, I_M$.

An alternative approach for regularization is to define an (L+M)×M-dimensional augmented plant $\underline{G}(z)$:

$$\underline{G}(z)=\begin{pmatrix} G(z) \\ G_{reg}(z) \end{pmatrix} \tag{20}$$

The regularizing transfer function could be chosen as $$G_{reg}(z)=\sqrt{\beta} I_M \tag{21}$$

In that case the quadratic form of the secondary path becomes $$\underline{G}^*(z)\underline{G}(z)=G^*(z)G(z)+\beta I_M \tag{22}$$

Figure 4:
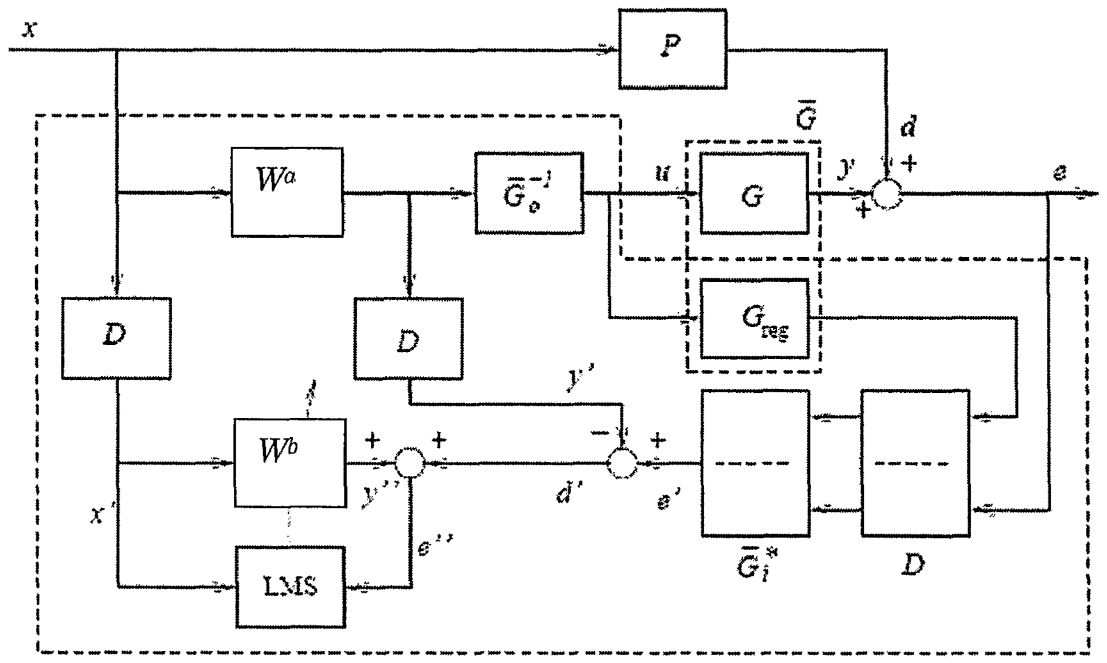
FIG. 4 illustrates an embodiment of the filter apparatus according to the invention, implementing a regularized modified filtered-error adaptive control scheme.

The new M×M-dimensional outer factor $\underline{G}_o(z)$ will be regularized since $\underline{G}^*_o(z)\underline{G}_o(z)=\underline{G}^*(z)\underline{G}(z)$. However, if the modified inner factor $\tilde{G}_i(z)$ is computed from $\tilde{G}_i(z)=G(z)\underline{G}^{-1}_o(z)$ then, in general, still $\tilde{G}^*_i(z)\tilde{G}_i(z)\neq I_M$. Therefore, also in this case, the derivation of the modified filtered-error scheme is no longer valid. However, this regularization strategy can still be useful for the post conditioned filtered-error scheme of FIG. 2. A solution for regularization in which the modified inner factor is all-pass is to incorporate the full (L+M)×M-dimensional augmented plant $\underline{G}(z)$ in the control scheme, as well as the full (L+M)×M dimensional inner factor $\underline{G}_i(z)$ and the M×M-dimensional outer factor $\underline{G}_o(z)$ such that $\underline{G}_i(z)\underline{G}_o(z)=\underline{G}(z)$, as obtained from an inner-outer factorization. The corresponding control scheme can be found in FIG. 4. The resulting scheme provides a solution for regularization of the inverse of the outer-factor using a regularized post-conditioning operator $\underline{G}^{-1}_o(z)$, while ensuring that the derivation of the modified filtered-error scheme remains valid, being dependent on the all-pass property $\underline{G}^*_i(z)\underline{G}_i(z)=I_M$. The scheme of FIG. 4 is a generalized form in the sense that it allows the use of any transfer function $G_{reg}(z)$ for regularization, instead of the use of the simplified regularization term $G_{reg}(z)=\beta\, I_M$, as described above.

Simulation Results

Figure 5:
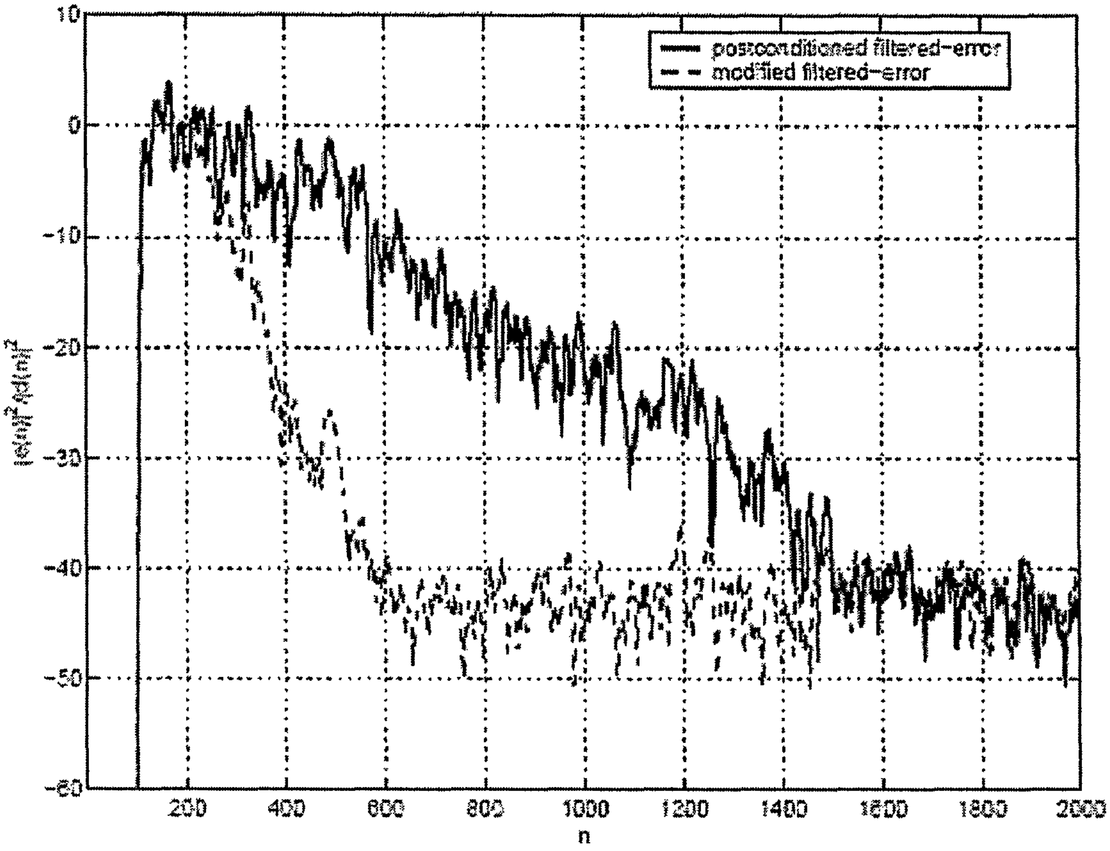
FIG. 5 illustrates a convergence difference between the filter apparatus according to the embodiment of FIG. 2 and according to the inventive embodiment of FIG. 4.
Figure 6:
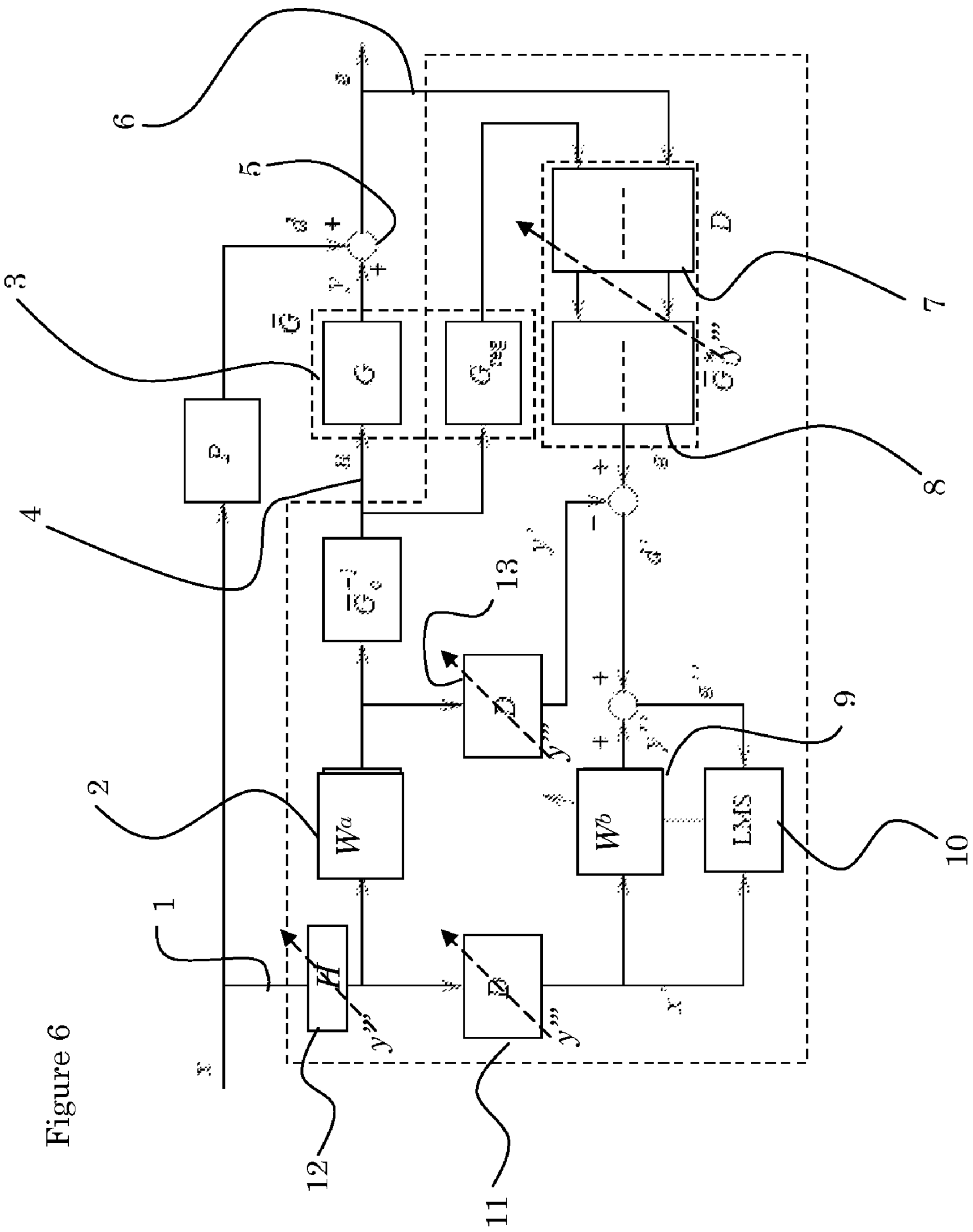
FIG. 6 illustrates the embodiment of FIG. 3 having a preconditioning circuit.

A simulation example is given for a single channel system, in which K=L=M=1. The number of coefficients for the controller was 20, the impulse response of G was that due to an acoustic point source corresponding to a delay of 100 samples, and J was set to 99. In FIG. 5, a comparison is given between the preconditioned filtered-error scheme, for which the convergence coefficient was set to the maximum of about 0.0025 and the modified filtered-error scheme, for which the convergence coefficient was set to the maximum of about 0.025. It can be seen that modified filtered-error scheme converges substantially faster than the preconditioned filtered-error scheme. The final magnitude of the error signal for large n is similar for both algorithms. The algorithm also has been implemented for multichannel systems; also for the multichannel systems the convergence improved by using the new algorithm. Various extensions of the algorithm are possible. The algorithm could be extended with a part which cancels the feedback due to the actuators on the reference signals, enabling feedback control based on Internal Model Control. Another possible extension is a preconditioning of the reference signals, in order to improve the speed of convergence for the case that the spectrum of the reference signal is not flat. As an example of this, FIG. 6 shows such a circuit. For the configuration of FIG. 6, the filter structure H (FIG. 7) flattens the spectrum of the reference signal if the mean-square value of the signal x is minimized. A preferred embodiment uses an adaptive filter for automatic adjustment of the filter K to changing spectra, for example by using an LMS-type adaptation for a FIR filter implementing K.

Figure 7:
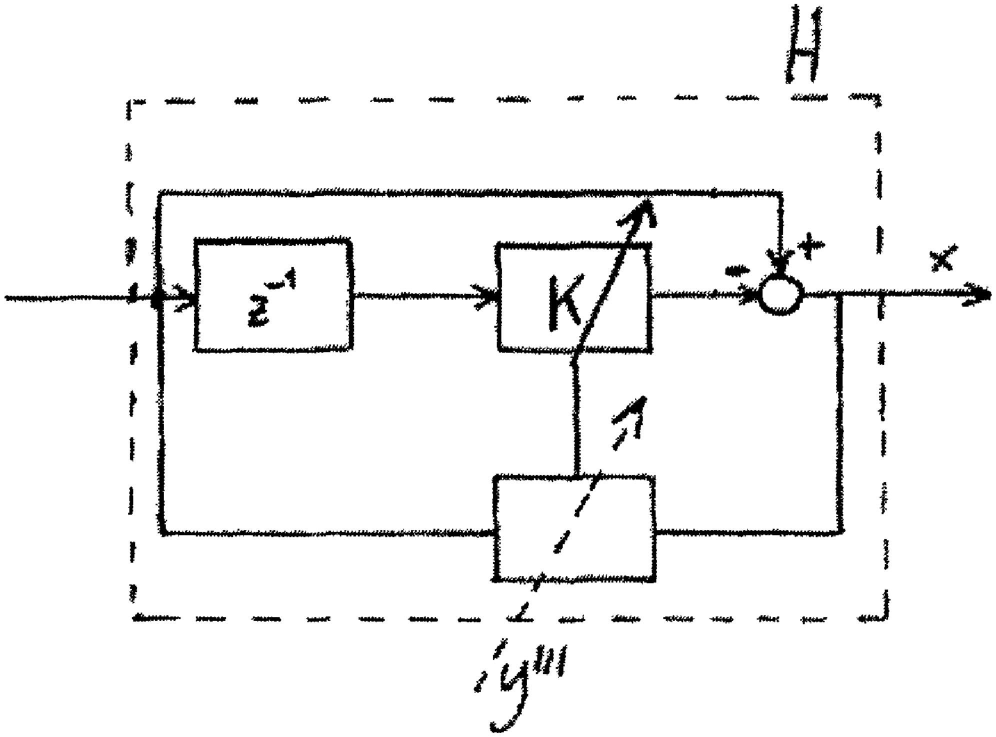
FIG. 7 illustrates an embodiment of the preconditioning circuit according to FIG. 6.

One embodiment of such a preconditioning circuit is shown in FIG. 7. Here a whitening filter H is provided for preconditioning of the reference signal x based on a unit-delay operator, a shaping filter K and a bypass. In particular, this adaptive circuit configuration minimizes the output of the whitening filter. A preferred way of controlling the rate of convergence of the whitening filter is as a function of the magnitude of the signal y'''=y'−y''. In addition, or alternatively, the magnitude of the signal y'''=y'−y'' can be used to give a decision regarding the necessity to change the number of samples delay in D and the length of Gi* and that adjusts the number of samples delay in D and the filter length of Gi*. In FIG. 6, the time reversed secondary path filter is physically implemented as a combination of the delay D and the length of Gi*, schematically indicated by dotted lines. This filter can be adapted as a function of said difference of control signal y'' and delayed control signal y'.

Preferably, the setting of the number of samples of the delay operators D and the number of samples of Gi* depends on the stationarity of the signals, in particular the reference signals and the disturbance signals. Thus, if the latter signals are to be regarded as nonstationary then preferably the delay D is reduced, leading to improved tracking performance and improved noise reduction. In one aspect, the signal y'''=y'−y'' may give a measure of nonstationary of the reference signal x and disturbance signal d. In case of perfectly stationary signals y''' will be small. If y''' is higher then the reference signals and disturbance signals may be instationary. As a consequence y''' can be used to decide whether the number of samples delay has to be modified. At a suitable time instant the delay can then be modified. Furthermore, additionally, or alternatively, tracking performance is also improved if the convergence coefficient of the whitening filter is increased. For instationary signals the convergence coefficient should be high for good tracking performance. However, high convergence coefficients may introduce a bias error, leading to suboptimal noise reductions. Therefore, for stationary signals, the convergence coefficient is preferably small. Preferable, the setting of the convergence coefficient will be adjusted on the basis of the magnitude of y''', as with the setting of the number samples in the delay blocks D.

In the above a multi-channel feedforward adaptive control algorithm is described which has good convergence properties while having relatively small computational complexity. This complexity is similar to that of the filtered-error algorithm. In order to obtain these properties, the algorithm is based on a preprocessing step for the actuator signals using a stable and causal inverse of the transfer path between actuators and error sensors, the secondary path. The latter algorithm is known from the literature as postconditioned filtered-error algorithm, which improves convergence speed for the case that the minimum-phase part of the secondary path increases the eigenvalue spread. However, the convergence speed of this algorithm suffers from delays in the secondary path, because, in order to maintain stability, adaptation rates have to be lower for larger secondary path delays. By making a modification to the postconditioned filtered-error scheme, the adaptation rate can be set to a higher value. Consequently, the new scheme also provides good convergence for the case that the secondary path contains significant delays. Furthermore, an extension of the new scheme is given in which the inverse of the secondary path is regularized in such a way that the derivation of the modified filtered-error scheme remains valid.

REFERENCES

[1] E. A. Wan, "Adjoint LMS: an efficient alternative to the filtered-X LMS and multiple error LMS algorithms," in Proc. Int. Conf. on Acoustics, Speech and Signal Processing ICASSP96 (IEEE, Atlanta, 1996), pp. 1842-1845.

[2] E. Bjarnason, "Analysis of the Filtered-X LMS algorithm," IEEE Transactions on Speech and Audio Processing 3, 504-514 (1995).

[3] S. Douglas, "Fast Exact Filtered-X LMS and LMS Algorithms for Multichannel Active Noise Control," in Proc. IEEE International Conference on Acoustics, Speech and Signal Processing ICASSP97 (IEEE, Munich, 1997), pp. 399-402.

[4] S. J. Elliott, "Optimal controllers and adaptive controllers for multichannel feedforward control of stochastic disturbances," IEEE Transactions on Signal Processing 48, 1053-1060 (2000).

[5] M. Vidyasagar, Control system synthesis: A factorization approach (MIT Press, Boston, 1985).

The following reference numerals are found in FIG. 6.

1. reference signal connector
2. first control filter
3. secondary source
4. secondary source signal connector
5. sensor
6. sensor connector
7. first delay
8. time reversed secondary path filter
9. second control filter
10. adaptation circuit
11. second delay
12. preconditioning circuit
13. third delay

The invention claimed is:

1. An active noise reducing filter apparatus for actively reducing noise d from a primary noise source x, comprising:

a secondary source signal connector for connecting to at least one secondary source, such as a loudspeaker, wherein said secondary source generates secondary noise y to reduce said primary noise d;

a sensor connector for connecting to at least one sensor, such as a microphone, for measuring said primary and secondary noise as an error signal e;

a first delay connected to said sensor connector for delaying said error signal e and a time reversed secondary path filter G* for providing a delayed filtered error signal e';

a reference signal connector for receiving at least one reference signal x, said reference signal x being coherent with said primary noise d;

a first control filter $W^a$ connected to said reference signal connector for receiving said reference signal x and for calculating a control signal from said reference signal for providing a secondary source signal u;

a second delay connected to said reference signal connector for receiving said reference signal x and for calculating a delayed reference signal x'; and an adaptation circuit arranged to adapt said first control filter $W^a$ based on said delayed reference signal x' and an error signal e"

wherein the filter apparatus further comprises:

a third delay connected to said first control filter $W^a$ for receiving said control signal and for calculating a delayed control signal y';

a second control filter $W^b$ connected to said second delay for receiving said delayed reference signal x' and for calculating an auxiliary control signal y"; wherein said adaptation circuit is connected to said second control filter for adapting said second control filter $W^b$ while receiving said error signal e" as a sum of said auxiliary control signal y" and an auxiliary noise signal d', said auxiliary noise signal d' constructed from a difference of said delayed filtered error signal e' and said delayed control signal y'; wherein for adapting said first control filter $W^a$ said adaptation circuit is arranged to update said first control filter $W^a$ by a copy of said updated second control filter $W^b$; and a flatness improving preconditioning circuit for preconditioning the reference signals.

2. A filter apparatus according to claim 1, further comprising:

an outer-factor inverse $G_0^{-1}$ connected to said first control filter for receiving said control signal and for calculating said secondary source signal u; wherein said outer-factor inverse is obtained by computing the inverse of an outer-factor, wherein said outer-factor is obtained from an inner-outer factorization of an open loop transfer path between said secondary source signal u and said error signal e; and wherein said time reversed secondary path filter is provided by a time-reverse and transpose of said inner-factor $G_i$.

3. A filter apparatus according to claim 2, further comprising a regularized outer-factor inverse $G_o^{-1}$ and a regularized inner factor $G_i^*$, wherein said reguralization is provided by an augmented transfer path filter $G_{reg}(z)$ for augmenting said secondary source G to define an (L+M)×M-dimensional augmented plant G(z):

$$\underline{G}(z) = \begin{pmatrix} G(z) \\ G_{reg}(z) \end{pmatrix}$$

4. A filter apparatus according to claim 3, wherein said transfer path filter function is chosen as $$G_{reg}(z)=\sqrt{\beta} I_M$$

where $I_M$ is an M×M unity transfer function.

5. A filter apparatus according to claim 1, wherein said preconditioning circuit is adapted as function of a difference of control signal y" and delayed control signal y'.

6. A filter apparatus according to claim 1, wherein said first, second and third delays are adapted as a function of said difference of control signal y" and delayed control signal y'.

7. A filter apparatus according to claim 2, wherein said time reversed secondary path filter is adapted as a function of said difference of control signal y" and delayed control signal y'.

* * * * *